United States Patent [19]

Olney

[11] Patent Number: 5,629,307
[45] Date of Patent: May 13, 1997

[54] USE OF IBOGAINE IN REDUCING EXCITOTOXIC BRAIN DAMAGE

[76] Inventor: John W. Olney, 1 Lorenzo La., St. Louis, Mo. 63124

[21] Appl. No.: 398,731

[22] Filed: Mar. 6, 1995

Related U.S. Application Data

[63] Continuation-in-part of Ser. No. 877,839, May 1, 1992, which is a continuation-in-part of Ser. No. 467,139, Jan. 18, 1990, abandoned, which is a continuation-in-part of Ser. No. 424,548, Oct. 20, 1989, Pat. No. 5,034,400.

[51] Int. Cl.$^6$ .................. A61K 31/55; A61K 31/54; A61K 31/44; A61K 31/135
[52] U.S. Cl. .................. 514/214; 514/226.2; 514/280; 514/282; 514/304; 514/315; 514/646
[58] Field of Search .................. 514/214, 282, 514/280, 304, 315, 226.2, 646

[56] References Cited

U.S. PATENT DOCUMENTS

| | | | |
|---|---|---|---|
| 4,499,096 | 2/1985 | Lotsof | 514/214 |
| 4,587,243 | 5/1986 | Lotsof | 514/214 |
| 4,857,523 | 8/1989 | Lotsof | 514/214 |
| 5,026,697 | 6/1991 | Lotsof | 514/214 |
| 5,034,400 | 7/1991 | Olney | 514/315 |
| 5,152,994 | 10/1992 | Lotsof | 424/436 |

OTHER PUBLICATIONS

Deecher, D.C., et al, "Mechanisms of action of ibogaine and harmaline congeners based on radioligand studies," *Brain Res.* 571: 242–247 (1992).

Glick, S.D., et al, "Effects and aftereffects of ibogaine on morphine self-administration in rats," *Eur. J. Pharmacol.* 195:341–435 (1991).

Glick, S.D., et al, "Local effects of ibogaine on extracellular levels of dopamine and its metabolites in nucleus accumbens and striatum," *Brain Res.* 628:201–208 (1993).

Popik, P., et al, "The putative anti-addictive drug ibogaine is a competitive inhibitor of[$^3$H]Mk–801 binding to the NMDA receptor complex,"*Psychopharmacology* 114:672–674 (1994).

Sershen, H., et al, "Ibogaine antagonizes cocaine-induced locomotor stimulation in mice," *Life Sci* 50:1079–86 (1992).

Sershen, H., et al, "Ibogaine reduces preference for cocaine consumption in C57BL/6By mice," *Pharmacol Biochem Behav* 47:13–19 (1994).

Green et al., "Antinociception opioids and the cholinergic System; Prog. Neurobiol.", (1986) 26/2 (119–146) see abstract.

*Primary Examiner*—Kevin E. Weddington
*Attorney, Agent, or Firm*—Patrick D. Kelly

[57] ABSTRACT

This invention discloses that ibogaine, a plant derivative, can be used as a safe NMDA antagonist at relatively high dosages (including dosages high enough to cause hallucinations), to reduce or prevent excitotoxic brain damage due to stroke, cardiac arrest, trauma or other forms of neuronal injury or degeneration, without causing the neurotoxic side effects caused by other NMDA antagonist drugs. The relative safety of ibogaine is due to antagonist activity at neuronal sigma receptors, which had not been known prior to discovery by the Applicant. This invention also discloses that ibogaine also can be administered in combination with (1) drugs that suppress activity at muscarinic acetylcholine receptors, or (2) drugs which suppress activity at the kainic acid subclass of glutamate receptors, to reduce or avoid the hallucinatory effects of ibogaine and provide a higher level of neuroprotective activity.

5 Claims, 1 Drawing Sheet

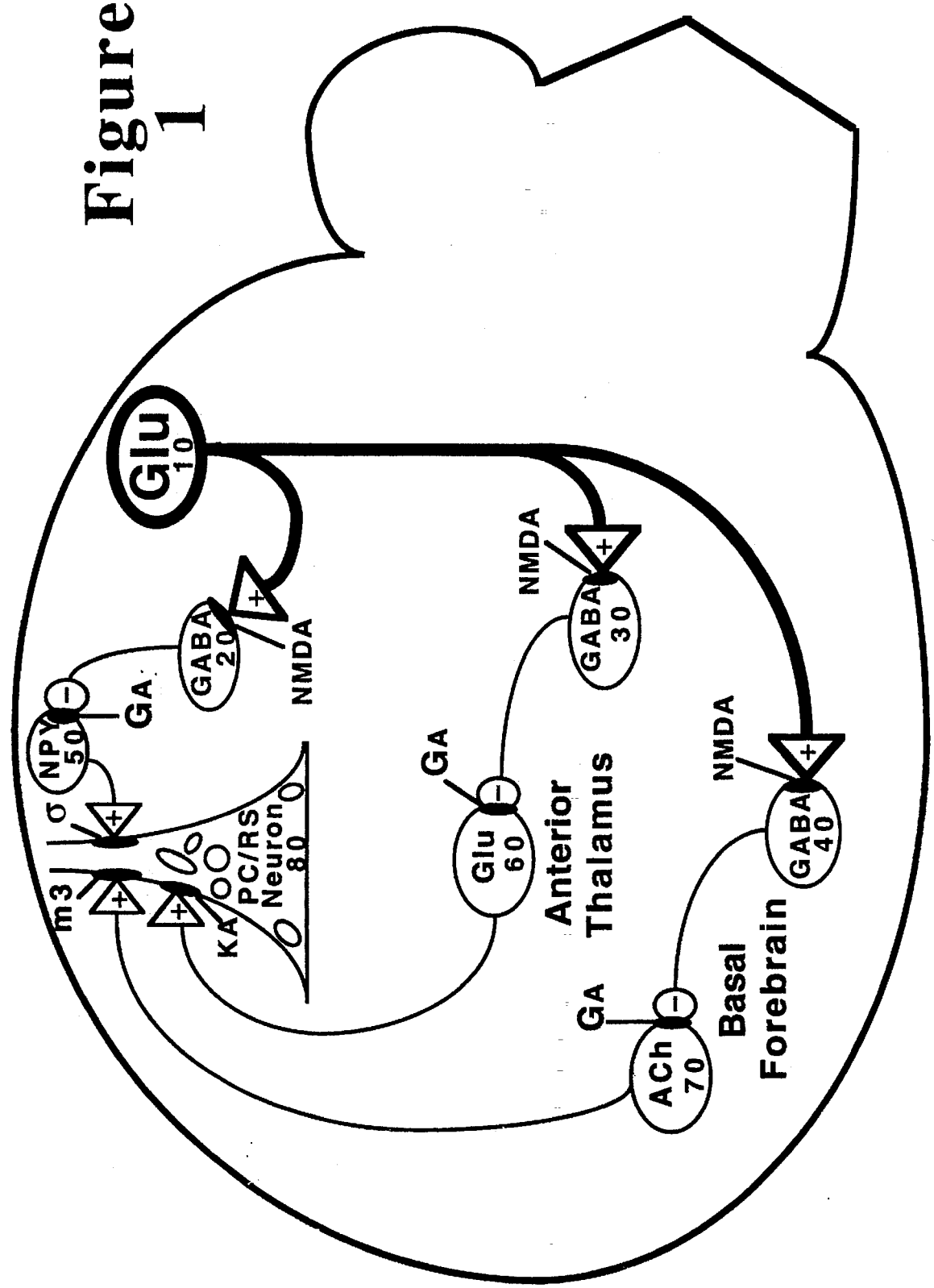

USE OF IBOGAINE IN REDUCING EXCITOTOXIC BRAIN DAMAGE

GOVERNMENT SUPPORT

The inventor's research is partially funded by a Career Research Scientist Award from the National Institutes of Health. Accordingly, the federal government may have certain rights in this invention.

RELATED APPLICATIONS

This application is a continuation-in-part of U.S. application Ser. No. 07/877,839, filed on May 1, 1992, currently on appeal, which was a continuation-in-part of U.S. application Ser. No. 07/467,139, filed on Jan. 18, 1990, now abandoned, which was a continuation-in-part of U.S. application Ser. No. 07/424,548, filed on Oct. 20, 1989, which issued as U.S. Pat. 5,034,400.

BACKGROUND OF THE INVENTION

Ibogaine is a drug found in the roots of *Tabernanthe iboga*, a shrub from Gabon, in equatorial west central Africa. Ibogaine has been known since the 1800's as an agent which at low doses has psychostimulant properties, and at high doses can induce a hallucinatory (oneirophrenic) state. For this reason it has been used in the Gabonese society for initiation ceremonial rites.

Ibogaine has also been used as an adjunctive agent in psychotherapy and psychoanalysis, and more recently has been described as an agent that may be able to suppress symptoms of dependence or withdrawal from addictive drugs. Discovery of this property of ibogaine led to the issuance of a number of U.S. patents to Howard S. Lotsof, including U.S. Pat. No. 4,499,096 (issued in 1985, concerning heroin addiction), U.S. Pat. No. 4,587,243 (issued in 1986, concerning cocaine and amphetamine abuse), U.S. Pat. No. 4,857,523 (issued in 1989, concerning alcohol abuse), U.S. Pat. No. 5,026,697 (issued in 1991, concerning tobacco and nicotine), and U.S. Pat. No. 5,152,994 (issued in 1992, concerning people suffering from multiple drug dependencies).

Lotsof's assertions regarding the usefulness of ibogaine in reducing various types of drug dependencies are consistent with evidence generated in several studies on laboratory animals. For example, in rats, ibogaine reduces morphine self-administration and ameliorates symptoms associated with morphine withdrawal and decreases preference for cocaine consumption; see, e.g., Glick et al 1991, Glick et al 1992, Sershen et al 1992, Cappendijk and Dzoljic 1993, and Sershen et al 1994 (full citations to articles are provided below).

Additional information on various cellular mechanisms involved in ibogaine's activity are provided in Deecher et al 1992, Sershen et al 1992, Glick et al 1993, and Popik et al 1994. For example, it appears that ibogaine inhibits binding to a dopamine transporter site (Sershen et al 1992), to a kappa opioid receptor site (Deecher et al 1992), to a voltage-dependent sodium channel site (Deecher et al 1992), and to an NMDA glutamate receptor ion channel site (Popik et al 1994). It is not clear what functional significance these findings may have, because the studies were conducted using receptor binding assays, and a serious limitation of such assays is that they shed no light on whether an agent acts as an agonist or antagonist, or, indeed, whether its binding activity might produce a mixture of agonist and antagonist effects which cancel out to yield no net effect on receptor function.

The recent report by Popik et al (1994) that ibogaine inhibits binding to an NMDA receptor ion channel site is of special interest in relation to the potential of ibogaine for counteracting drug dependencies. Although the evidence from the Popik et al receptor binding study does not clarify what type of action it may have at the NMDA subtype of glutamate receptor, it has been reported recently that agents which are known antagonists of NMDA receptors can prevent the development of tolerance to opiate analgesics (see Marek et al 1991; Trujillo and Akil 1991; Ben-Eliyahu et al 1992; Tal and Bennett 1993), to benzodiazepine anxiolytics such as diazepam (sold under the trade name VALIUM; Turski et al, PCT patent application WO 94/01094), to cocaine (Pudiak and Bozarth 1993), and to alcohol (Wu et al 1993). Accordingly, it was postulated in Popik et al 1994 that the action of ibogaine in blocking drug tolerance, craving, and dependence may signify that it acts as an antagonist at NMDA receptors.

The Applicant has conducted recent experiments using functional bioassay techniques demonstrating unequivocally that ibogaine does act as an antagonist at NMDA receptors, and that it also acts as an antagonist at sigma receptors. Both of these discoveries are important aspects of this invention, and have not been previously reported.

In addition, the present invention pertains, not to blocking drug addiction mechanisms, but to an entirely separate and distinct use for ibogaine, which involves the reduction or prevention of brain damage caused by ischemia (inadequate blood flow to the brain, as occurs during stroke, cardiac arrest, and trauma), hypoxia (inadequate oxygen supply to the brain, as occurs during suffocation, drowning, carbon monoxide poisoning, etc.), and certain other types of crises or conditions. These crises or conditions generate a process in the central nervous system (CNS) known as "excitotoxicity". Since this subject is complex, additional information is provided below on excitotoxicity, on the role of glutamate as an essential neurotransmitter under healthy conditions and as a deadly neurotoxin under certain abnormal conditions, and on the roles of NMDA receptors and NMDA antagonist drugs under such conditions. This is a brief overview; additional information on these topics is provided in numerous articles and books, including Choi 1988 and Olney 1989 (review articles) and in the multi-volume treatise on the central nervous system edited by Adelman (either the 1987 or the 1995 edition).

Additional newly-developed information on the neuronal circuitry described herein is provided in a co-pending U.S. patent application, Ser. No. 08/381,334, co-invented by the same Applicant herein, entitled "USE OF ALPHA-2 ADRENERGIC DRUGS TO PREVENT ADVERSE EFFECTS OF NMDA RECEPTOR HYPOFUNCTION". The contents of that application are incorporated herein by reference; if that co-pending application has not yet issued as a patent, then it will be opened for public inspection and copying upon issuance of a patent based upon this instant application.

The Glutamate Neurotransmitter System

Glutamate (Glu) is recognized as the predominant excitatory neurotransmitter (messenger molecule) in the mammalian central nervous system (CNS); for a review, see the chapter by Olney entitled "Glutamate" in *The Encyclopedia of Neuroscience*, edited by Adelman (either the 1987 or the 1995 edition).

Glu is involved in transmitting messages from one nerve cell (neuron) to another in many different circuits within the CNS, and therefore serves many important functions. Glu mediates these functions by being released from a sending neuron onto a receptor at a synapse on the surface of a receiving neuron. A synapse is a signal-transmitting junction between two neurons. Binding of Glu to the synaptic receptor initiates signal transfer by opening an ion channel and triggering ionic currents. This is considered an excitatory process, because it stimulates an increased level of electrochemical activity in the receiving neuron.

NMDA and non-NMDA Subtypes of Glutamate Receptors

There are several different subtypes of receptors through which Glu transmits messages. A particularly important receptor through which Glu mediates a wide range of functions is the N-methyl-D-aspartate (NMDA) receptor, which is so called because NMDA, a molecule structurally related to Glu, is highly selective and potent in activating this receptor (reviewed by Watkins 1987 and Olney 1989). Other major classes of Glu receptors are kainic acid receptors and Quis/AMPA receptors; these two classes are often referred to collectively as non-NMDA receptors. Both NMDA and non-NMDA receptors are normally activated by Glu and are ordinarily referred to as Glu receptors although they are also activated to a lesser extent by aspartate, a related excitatory amino acid. Glu receptors are also sometimes referred to generically as excitatory amino acid (EAA) receptors.

Antagonist Drugs that Block NMDA Receptors

As will be described below, antagonist drugs that block Glu receptors offer great promise as therapeutic agents. Therefore, drug companies have recently begun developing drugs that block glutamate receptors. Initially, the major emphasis was on developing drugs that block NMDA receptors and two broad classes of such compounds are now available. One class is referred to as competitive NMDA antagonists; these agents bind at the NMDA/GLU binding site (such drugs include CPP, D-CPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Another class is referred to as non-competitive NMDA antagonists; these agents bind at other sites in the NMDA receptor complex (such drugs include phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715). For reviews, citations, and chemical structures, see, e.g., Rogawski 1992 and Massieu et al 1993, and articles cited therein.

Toxic Effects of Excessive Glu Activity; Utility of NMDA Antagonist Drugs

In addition to its many beneficial functions, the Glu molecule harbors treacherous neurotoxic potential. Glu neurotoxicity is referred to as "excitotoxicity" because the neurotoxic action of Glu, like its beneficial actions, is mediated by an excitatory process (reviewed by Olney 1990 and Choi 1992). Ordinarily, when Glu is released at a synaptic receptor, it binds only transiently to the receptor then is rapidly removed from the receptor region by a transport process that transports Glu back inside a cell. Under certain abnormal conditions, including stroke, epilepsy and CNS trauma, the Glu uptake process fails and Glu accumulates at the receptor and persistently excites electrochemical activity until it literally excites to death neurons that have Glu receptors. Since almost all of the neurons in the CNS have Glu receptors, this mechanism can trigger an enormous amount of CNS damage.

As used herein, the term "acute CNS injury" includes ischemic events (which involve inadequate blood flow, such as a stroke or cardiac arrest), hypoxic events (involving inadequate oxygen supply, such as drowning, asphyxiation, or carbon monoxide poisoning), trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (reviewed by Choi 1988 and Olney 1990).

CNS trauma represents a special situation in which excessive activity at NMDA receptors can cause neuronal damage by both a direct and indirect mechanism. Persistent activation of NMDA receptors can directly excite neurons to death but, in addition, the hyperexcitation process involves excessive influx of charged ions into CNS cells which creates an osmotic imbalance that causes abnormal amounts of water to flow in with the ions, the net result being excessive swelling of millions of CNS cells and increased intracranial pressure (because the bony cranial vault is inflexible and cannot expand to accommodate the increased volume of the swollen cells). Elevated intracranial pressure represents an indirect mechanism that contributes significantly to both morbidity and mortality in CNS trauma victims, and NMDA antagonists are useful not only in preventing direct excitotoxic damage but in reducing increased intracranial pressure and thereby preventing indirect damage.

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis (Lou Gehrig's disease), AIDS dementia, Parkinson's disease and Huntington's chorea (Olney 1990). It is considered likely that NMDA antagonists will prove useful in the therapeutic management of such chronic diseases.

Toxic Effects of Excessive Glu Activity; Utility of non-NMDA Antagonist Drugs The toxic effects of excessive Glu activity have been described in detail above. As mentioned above, when agents that selectively block non-NMDA Glu receptors became available, they were tested for efficacy in protecting against ischemic neuronal degeneration in several animal ischemia models and were found to be at least as effective and in some cases more effective than NMDA antagonists. The non-NMDA antagonist NBQX has also been shown to be effective in preventing neuronal degeneration associated with brain trauma. Non-NMDA antagonists that penetrate blood CNS barriers have not been available for a long enough time to allow them to be tested for neuroprotective efficacy against all types of neuropathological conditions involving excessive Glu activity. However, it is considered likely that they will be found effective in many such conditions, because many neurons in the CNS have both NMDA and non-NMDA receptors and therefore are vulnerable to excitotoxic degeneration mediated through either class of receptor whenever excessive Glu comes in contact with such receptors.

NMDA Antagonist Drugs: Both Beneficial and Detrimental

As described above under the heading, "Utility of NMDA Antagonist Drugs", NMDA antagonists can have several important beneficial effects. However, despite these beneficial effects, NMDA antagonists can also cause serious detrimental side effects which manifest as neurotoxic changes in CNS neurons and as psychotomimetic symptoms (described in the immediately following paragraph). As described in Olney et al 1989b, and in U.S. Pat. No. 5,034,400 (Olney 1991), the neurotoxic changes include the formation of vacuoles and dissolution of mitochondria in large neurons in the posterior cingulate and retrosplenial (PC/RS) regions of the cerebral cortex of adult rats. These changes are detected histologically within 2 to 4 hours following a single subcutaneous treatment with either competitive or non-competitive NMDA antagonists (Olney et al 1991). Twenty four hours after NMDA antagonist treatment, the vacuolar changes are diminished but new changes in the form of abnormal expression of heat shock protein (HSP) appear and the HSP changes remain detectable for up to 2 weeks after NMDA antagonist treatment. While all of the above changes occur following treatment with a relatively low dose of an NMDA antagonist, higher doses have been shown to kill neurons not only in the PC/RS cortex but in several other neocortical and limbic brain regions (Corso et al 1994; Fix et al 1993). In addition, it has been shown that subchronic treatment with daily injections of an NMDA antagonist for 3–5 days causes neuronal cell death in the PC/RS and other cortical and limbic brain regions (Corso et al 1992; Ellison and Switzer 1993; Horvath and Buzsaki 1993). It has been shown that both competitive and non-competitive NMDA antagonists cause both the vacuolar reaction and death of cerebrocortical neurons.

In addition to these neurotoxic changes in neurons of the adult rat brain, NMDA antagonists are known to cause psychotomimetic effects in adult humans (reviewed by McCarthy 1981). These psychotomimetic effects were first observed many years ago in patients treated with phencyclidine, a drug that was introduced into human medicine as an anesthetic in the late 1950s. This was long before it was known that phencyclidine acts as an NMDA antagonist, in fact long before NMDA receptors were first described. In this early period, phencyclidine was introduced as an anesthetic agent and it was found immediately that patients anesthetized with phencyclidine displayed psychotic symptoms (termed an "emergence reaction") when they were coming out from under the anesthesia. Because these psychotomimetic side effects were quite severe, phencyclidine was immediately withdrawn from use in clinical medicine. Subsequently, phencyclidine became well known as a widely abused illicit hallucinogenic street drug (angel dust, PCP).

In the 1980's it was discovered that the site of action of PCP in the CNS is at a "PCP recognition site" within the ion channel of the NMDA Glu receptor. At this site, PCP acts as a non-competitive antagonist that blocks the flow of ions through the NMDA ion channel. Thus, PCP and related agents such as ketamine and MK-801 that also act at the PCP site became known as non-competitive NMDA antagonists. Since ketamine, a drug currently used in human anesthesia, is known to cause "emergence reactions" similar to but not as severe as those caused by PCP, it became evident to researchers in the late 1980s that all drugs acting at the PCP site as non-competitive NMDA antagonists were likely to have psychotomimetic side effects. This caused pharmaceutical companies to shift their focus away from non-competitive agents acting at the PCP site to competitive NMDA antagonists acting at the NMDA recognition site. However, in the last few years three competitive NMDA antagonists (CPP, CPPene, CGS 19755) have been administered in relatively low doses to adult human subjects and all three of these agents induced a psychotomimetic reaction (Kristensen et al 1992; Herrling 1994; Grotta 1994). Therefore, it is now recognized that various competitive NMDA antagonists and various non-competitive NMDA antagonists all cause the same pathomorphological effects in rat brain (Olney et al 1991; Hargreaves et al 1993) and also have psychotomimetic effects in humans (Kristensen et al 1992; Herrling 1994; Grotta 1994). Thus, it seems likely that these two types of side effects are morphological and psychological manifestations of the same toxic process and that the ability of a given agent to produce these adverse effects does not depend on the site within the NMDA receptor channel complex where it binds, but on the efficacy with which it blocks the functional activity of this receptor channel complex. In practical terms, a major obstacle to the use of NMDA antagonists as neurotherapeutic drugs lies in their potential for inducing adverse CNS side effects, including both brain damage and psychosis.

Status of NMDA Receptor Antagonists as Neurotherapeutic Drugs

Despite the remarkable neuroprotective and other potential neurotherapeutic effects of NMDA antagonists, no agent in this category has gained approval from FDA for human clinical use, the major problem being that all agents in this class that have been tested thus far have been found to have the above-mentioned neurotoxic and psychotomimetic side effects. Therefore, FDA has either placed a moratorium on the further clinical testing of such compounds or has restricted clinical trials to an evaluation of exceedingly low doses which have very little chance of proving to be therapeutically effective.

Several types of drugs that can reduce or prevent the neurotoxic side effects of NMDA antagonists have been described (e.g., Olney et al 1991). However, there is a great deal of resistance in the pharmaceutical industry to the use of drug combinations because it is vastly more expensive to gather the requisite toxicological data to establish the safety of multiple drugs used in combination than to establish the safety of a single drug. Of equal importance is the fact that the chances are great that after millions of dollars are invested in demonstrating the safety of a drug combination in experimental animals, it will finally be found that humans cannot tolerate the combined side effects of such a complex medical regimen. Thus, progress in this important drug development area has come nearly to a standstill at the present time.

One potential resolution of the problem would be if a single molecule could be found that has potent NMDA antagonist properties without accompanying neurotoxic side effects. Progress toward development of such molecules has heretofore not been promising. In fact, every NMDA antagonist introduced into clinical trials thus far has been shown to produce severe psychotic reactions at relatively low doses. This immediately engenders the suspicion that these agents may also cause injury and/or death of cerebrocortical neurons in humans, as they have been shown to do in experimental animals.

The Present Invention

One object of the present invention is to disclose that ibogaine decidedly is an NMDA antagonist that is effective in preventing NMDA receptor-mediated excitotoxic neurodegeneration.

Another object of this invention is to disclose that ibogaine can be administered to rats at high doses (in excess of doses required to block NMDA receptors) without causing any histological evidence of neuronal injury or cell death.

Another object of this invention is to disclose that ibogaine exerts antagonist activity at a sigma receptor. In light of additional experimental data gathered by the Applicant, this explains its lack of neurotoxic side effects; the blocking action of ibogaine at sigma receptors serves to prevent the neurotoxic side effects of its NMDA antagonist activity. Thus, this invention discloses that ibogaine is a potentially very useful neurotherapeutic drug which incorporates, within a single molecule, both (1) effective neuroprotective action against acute excitotoxic neuronal injury, and (2) a safener mechanism that protects against its own neurotoxic side effects.

An additional object of the present invention is to disclose that ibogaine can be administered together with a second drug (such as a muscarinic or non-NMDA antagonists or alpha-2 adrenergic agonists) to prevent the hallucinogenic side effects of ibogaine, without suppressing the beneficial anti-excitotoxic NMDA antagonist activity of ibogaine.

SUMMARY OF THE INVENTION

This invention discloses that ibogaine, a plant derivative, can be used as a safe NMDA antagonist at relatively high dosages (including dosages high enough to cause hallucinations), to reduce or prevent excitotoxic brain damage due to stroke, cardiac arrest, trauma or other forms of neuronal injury or degeneration, without causing the neurotoxic side effects caused by other NMDA antagonist drugs. The relative safety of ibogaine is due to antagonist activity at neuronal sigma receptors, which had not been known prior to discovery by the Applicant.

This invention also discloses that ibogaine can be used in combination with additional drugs such as (1) anticholinergic agents that suppress activity at muscarinic acetylcholine receptors, or (2) drugs which block the kainic acid subclass of glutamate receptors. Such drug combinations can reduce or avoid the hallucinatory effects of ibogaine, if desired.

BRIEF DESCRIPTION OF THE DRAWING

FIG. 1 is a schematic depiction of a neural circuit in the brain. In this circuit, the release of glutamate by neuron 10 stimulates other neurons (20–40) that release GABA, an inhibitory neurotransmitter. The GABA acts at still other neurons (50–70) in a manner that protects a pyramidal neuron in the posterior cingulate or retrosplenial (PC/RS) cortex against toxic overstimulation. Of particular interest is the sigma receptor on the surface of the pyramidal neuron; this sigma receptor is blocked by ibogaine as a secondary effect in a manner which helps protect the pyramidal neuron against vacuole formation and mitochondrial dissolution due to the NMDA antagonist activity of the ibogaine.

DESCRIPTION OF THE PREFERRED EMBODIMENTS

This invention discloses that ibogaine, a plant derivative, can be used as a safe NMDA antagonist at relatively high doses (including dosages high enough to cause hallucinations), to reduce or prevent excitotoxic brain damage without causing the toxic side effects caused by other NMDA antagonist drugs. The relative safety of ibogaine apparently is due to antagonist activity at neuronal sigma receptors, which had not been reported anywhere prior to discovery by the Applicant.

Neuroprotective Activity and NMDA Antagonist Properties

A recent report (Popik et al 1994) stated that ibogaine competitively inhibits the binding of MK-801 (dizocilpine maleate) to cell membranes isolated from rat forebrain tissue. Since MK-801 selectively binds to the PCP recognition site in NMDA receptor complexes, this report suggested that ibogaine may bind to the same PCP recognition site in the NMDA receptor complex where MK-801 binds. However, that piece of information did not provide any clue regarding the functional significance or the cellular effects of ibogaine after the binding reaction occurs; it did not indicate whether ibogaine exerts an agonist effect, an antagonist effect, or no net influence on the functioning of the NMDA ion channel.

To address that issue, the Applicant undertook studies involving chick embryo retinal tissue, described in Example 1, below. Briefly, this assay uses pieces of retinal tissue from chicken embryos, which have mature NMDA and non-NMDA receptors. Three different selective agonists (NMDA, kainic acid, and AMPA) were used to challenge tissue samples. Each of these agents selectively triggers neuronal activity via one type of Glu receptor without triggering the other types of Glu receptors.

In the absence of an NMDA antagonist such as MK-801, NMDA causes severe neuronal damage and necrosis in retinal tissue samples within 30 minutes. Ibogaine was found to block this NMDA neurotoxicity, while it showed no blocking activity against KA or AMPA neurotoxicity. This signifies that ibogaine is an NMDA antagonist, which can exert neuroprotective activity comparable to other known NMDA antagonists. The protection provided by ibogaine was concentration-dependent, and ranged from about 10 μM for substantial protection against 80 μM NMDA, up to about 25 μM for essentially complete protection against 80 μM NMDA. This potency can be regarded as moderate or weak when compared to other known NMDA antagonists; for example, in the same assay, phencyclidine is about ten times more potent, while MK-801 is about 50 times more potent.

To the best of the Applicant's knowledge, no other evidence has been published demonstrating that ibogaine is, in fact, an NMDA antagonist that can be used to protect against excitotoxic damage or death in neurons.

After analyzing the results of the in vitro chick embryo tests, the Applicant undertook a second set of in vivo tests in which ibogaine was injected intraperitoneally (ip) into adult female rats at 50 mg/kg. Based on the in vitro potency levels shown in Example 1, this is a relatively high dosage, which is believed by the Applicant to provide a high level of protection against excitotoxicity via NMDA antagonist activity. At this high dosage, the ibogaine did not cause any signs of vacuole formation, mitochondrial dissolution, or other cellular damage in the vulnerable posterior cingulate and retrosplenial cortical regions, or in any other cortical or limbic regions of the brain (all cortical and limbic regions were studied histologically). Separate groups of rats were studied by appropriate methods to search for vacuole reactions at 4 hours, heat shock protein expression at 24 hours, or neuronal necrosis at 4 days following ibogaine injection. None of these signs of toxicity, which are uniformly seen following administration of other NMDA antagonists at neuroprotective dosages, were seen following ibogaine administration.

Neuronal Circuitry and Disinhibition

As described in more detail in above-cited co-pending U.S. application Ser. No. 08/381,334, numerous agents with various neuronal receptor activities have been tested by the Applicant to help elucidate the role of different neuronal systems in the toxic side effects caused by NMDA antagonists. The neural circuit diagram in FIG. 1 is based on data gathered in those experiments, and it can help explain these toxic side effects in terms of a "disinhibition" mechanism.

The neural circuitry relevant to the present invention is depicted in a simplified schematic manner in FIG. 1. In this depiction, glutamate is released, in tiny amounts but on a continuous basis, by synapses that emerge from a neuron labelled as GLU neuron 10 in FIG. 1. Glutamate molecules being released by synapses which emerge from neuron 10 react with and activate NMDA receptors on the surfaces of three GABAergic neurons 20, 30, and 40. This slow and steady release of glutamate by neuron 10 provides a steady, continuous driving force that keeps GABAergic neurons 20, 30, and 40 in a constant state of activity, resulting in continuous release of GABA onto GABA inhibitory receptors on three different types of excitatory neurons that release Neuropeptide Y (NPY, from neuron 50), glutamate (from neuron 60), or acetylcholine (ACh, from neuron 70).

Thus, glutamate, via its driving action on GABAergic inhibitory neurons, exerts "tonic inhibition" (the word "tonic" implies that it maintains a constant level of inhibitory tone) which restrains the activity of three excitatory pathways which use NPY, glutamate, or ACh as excitatory neurotransmitters.

This represents an important principle (and an apparent paradox) of CNS activity. An excitatory neurotransmitter such as glutamate can cause suppression, rather than excitation, of neuronal activity.

This is important, not only for physiological functions in the CNS, but for understanding how "disinhibition" can contribute to neuronal damage and death when NMDA antagonists are used. If the NMDA receptors that govern GABAergic neurons 20, 30, and 40 in FIG. 1 are blocked by an NMDA antagonist, then the ability of neuron 10 to tonically inhibit the three excitatory neurons 50, 60, and 70 (via GABAergic neurons 20, 30, and 40) is lost. This loss of glutamate-mediated control is referred to herein as "disinhibition" of the inhibitory control mechanism that normally protects pyramidal neuron 80. When disinhibition occurs due to NMDA receptor hypofunction, all three excitatory neurons 50, 60, and 70 can begin to release undesirably high levels of their excitatory neurotransmitters.

All three of the excitatory neurons 50, 60, and 70 are coupled via axons to pyramidal neuron 80, located in the posterior cingulate or retrosplenial (PC/RS) cortex of the brain. If all three excitatory neurons 50, 60, and 70 begin firing simultaneously, they can overstimulate pyramidal neuron 80 and begin pushing it to the point where it becomes so exhausted that it can suffer serious damage and eventually die from overstimulation.

The pyramidal neuron 80 is shown as having three different types of excitatory receptors: (1) kainic acid receptors, a type of non-NMDA glutamate receptor; (2) m3 receptors, a type of muscarinic acetylcholine receptor; and, (3) sigma ( ) receptors, which are believed to be triggered by neuropeptide Y (NPY). The presence of all three types of excitatory receptors on pyramidal neurons is supported by the experimental evidence gathered by the Applicant.

After discovering that blockade of NMDA receptors can destroy the brain's inhibitory control of all three excitatory pathways (sigma, muscarinic, and kainic acid) that innervate PC/RS cerebrocortical neurons, the Applicant undertook a series of experiments to evaluate the relative importance of each of the three pathways. In these experiments, combinations of specific receptor agonists were microinjected into the cingulate cortex; this type of direct injection into the brain avoided problems of limited permeability through blood-brain barriers. The three test drugs were: (+)SKF-10, 047, an agonist that stimulates activity at sigma receptors; carbachol, an agonist that stimulates activity at muscarinic-type acetylcholine receptors; and kainic acid, an agonist which stimulates non-NMDA glutamate receptors of the kainic acid subtype. In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with any two (or only one) of the three drugs, no such toxic reaction was found.

These results corroborate the circuit diagram depicted in FIG. 1, and they indicate that NMDA antagonist neurotoxicity requires simultaneous hyperactivation of all three of these receptor systems (i.e., sigma receptors, muscarinic acetylcholine receptors, and kainic acid receptors).

A major implication of these results is that, in order to prevent this type of neurotoxic reaction caused by NMDA antagonists, blockade of any one of these three receptor systems (sigma, muscarinic, or kainic acid) can be sufficient.

Discovery that Ibogaine's Built-in Safener Mechanism Involves Antagonist Activity at Sigma Receptors Based on the Applicant's experimental finding that it requires activation of all three receptor systems (sigma, muscarinic, and kainic acid) for NMDA antagonist neurotoxicity to occur, the Applicant postulated that the absence of toxic side effects after ibogaine injection (described above and in Example 2) might signify that ibogaine, in addition to its NMDA antagonist activity, might also exert blocking activity at one of the three excitatory pathways that innervate pyramidal neurons (i.e., the muscarinic, sigma, or kainic acid pathways).

To test this possibility, the Applicant administered ibogaine (50 mg/kg, injected ip) together with a sigma agonist, (+)SKF-10,047 (50 mg/kg). This agent was chosen for the first test, since it crosses the BBB and can be injected subcutaneously without requiring injection directly into the brain, and since it activates fewer receptors than kainic acid or carbachol.

When coadministered with the sigma agonist (+)SKF-10, 047, ibogaine consistently caused a very prominent vacuole reaction in PC/RS cerebrocortical neurons. In control tests, administering (+)SKF-10,047 (50 mg/kg sc) by itself did not cause a vacuole reaction.

These findings indicate that (1) ibogaine blocks NMDA receptors, thereby causing disinhibition of the three excitatory pathways (muscarinic, sigma, and kainic acid) through which the vacuole reaction is normally mediated; but, (2) the vacuole reaction does not occur, since ibogaine also exerts a blocking action at sigma receptors.

These results further confirm (1) the Applicant's conclusion that it requires hyperactivation of all three receptor systems (sigma, muscarinic, and kainic acid) for the toxic side effect (vacuole formation) to occur, and (2) the corollary conclusion that blockade of only one of those three systems is sufficient to prevent the toxic side effect of NMDA antagonists.

Moreover, these results specifically identify blockade of the sigma receptor as the mechanism by which ibogaine avoids the neurotoxic side effects that other NMDA antagonists predictably cause.

Finally, these results also signify that ibogaine penetrates the blood-brain barrier and enters the CNS in sufficient quantities to effectively block NMDA receptors in a therapeutic manner.

From these discoveries, it follows that ibogaine can be used for neuroprotective therapy against neuronal disorders involving an excitotoxic mechanism. It can be used at high doses without risk of causing toxic side effects in cerebrocortical neurons, provided that it is not coadministered with drugs that activate the sigma receptor system.

In addition to the direct forms of excitotoxic overstimulation described in the Background section, excessive activity at NMDA receptors can also severely aggravate neuronal damage caused by trauma (mechanical injury) to the brain or spinal cord. Many trauma victims suffer from a dangerous and potentially lethal increase in intracranial pressure, which involves water flowing into neurons in an effort to sustain osmotic balance as charged ions flow into the neurons during neuronal excitation. Elevated intracranial pressure is a major cause of morbidity and mortality in CNS trauma victims, and ibogaine, as an NMDA antagonist, is potentially useful in reducing intracranial pressures following such crises.

As used herein, the term "acute insult to the central nervous system" includes short-term events which involve or pose a threat of neuronal damage mediated by excitotoxicity or other forms of excessive stimulation of neurons by glutamate. This includes ischemic events (which involve inadequate blood flow, such as a stroke or cardiac arrest), hypoxic events (involving inadequate oxygen supply, such as drowning, suffocation, or carbon monoxide poisoning), trauma in the form of mechanical or similar injury, certain types of food poisoning which involve an excitotoxic poison such as domoic acid, and seizure-mediated neuronal degeneration, which includes several types of severe epileptic seizures. As an NMDA antagonist which does not cause toxic side effects, ibogaine is a good candidate drug for protecting neurons in the CNS against any such damage.

In addition to neuronal damage caused by acute insults to the CNS, excessive activation of glutamate receptors may also contribute to more gradual neurodegenerative processes leading to cell death in various chronic neurodegenerative diseases, including Alzheimer's disease, amyotrophic lateral sclerosis (Lou Gehrig's disease), AIDS dementia, Parkinson's disease and Huntington's chorea (Olney 1990). It is considered likely that NMDA antagonists will prove useful in the therapeutic management of such chronic diseases, and ibogaine, as an NMDA antagonist that does not cause toxic side effects, is also a good candidate drug for preventing and reducing such gradual neurodegeneration.

Excessive activation of NMDA receptors is also responsible for the generation of "neuropathic" pain, a type of pain which is sometimes called "neurogenic pain" or "windup" pain (Woolf et al 1989; Kristensen et al 1992; Yamamoto and Yaksh 1992). Neuropathic pain is a chronic condition in which NMDA receptors in neural pain pathways have become "kindled" to an abnormally high level of sensitivity so that they spontaneously convey nerve messages that the patient perceives as pain even though no painful stimulus has been inflicted. By mechanisms that are poorly understood, pathological changes associated with diabetes are conducive to the generation of neuropathic pain, a condition known as "diabetic neuropathy". One of the distinguishing characteristics of neuropathic pain is that morphine and related pain-killing drugs which are effective in controlling other types of pain are usually ineffective in controlling neuropathic pain (Backonja 1994). Several recent reports indicate that NMDA antagonists can prevent or ameliorate neuropathic pain (Davar et al 1991; Mao et al 1992; Seltzer et al 1991; Neugebauer et al 1993; Kristensen et al 1992; Backonja et al 1994). Ibogaine, as an NMDA antagonist that does not cause toxic side effects, is a good candidate drug for preventing and reducing such neuropathic pain.

Based on additional research by the Applicant using drugs that act as agonists at the alpha-2 class of adrenergic receptors (this research is described in detail in the above-cited co-pending application 08/381,334, incorporated by reference), the Applicant believes that certain types of alpha-2 adrenergic agonists which apparently provide some relief from neuropathic pain, due to their own neuronal activities, may provide ideal agents for co-administration with ibogaine to relieve neuropathic pain (see, e.g., Puke and Wiesenfeld-Hallin 1993; Zeigler et al 1992; Danzebrink and Gebhart 1990). Such alpha-2 adrenergic agonists appear to provide excellent candidates for co-administration with ibogaine, for controlling neuropathic pain.

The term, "pathologic side effects in cerebrocortical neurons", as used in the claims, refers to any or all of the following side effects, which are produced in various cortical (and limbic) regions of mammalian brains by most types of NMDA antagonist drugs other than ibogaine: (a) formation of vacuoles in neurons in cerebrocortical brain regions; (b) expression of heat shock proteins in cerebrocortical brain regions; (c) alteration or loss of mitochondria in neurons; and (d) neuronal death. Unlike psychotomimetic symptoms such as hallucinations, pathologic side effects in cerebrocortical neurons can be quantitatively measured and evaluated in lab animals.

Use of A Second Agent to Avoid Psychotomimetic Effects

An additional implication of the findings described above pertains to the psychotomimetic actions of ibogaine. As described in more detail in above-cited co-pending U.S. patent application 08/381,334, the Applicant has developed considerable evidence indicating that the same Glu/GABA disinhibition mechanism which underlies and mediates the toxic (vacuolar) side effects of NMDA antagonists also appear to be intimately involved in the psychotomimetic actions (hallucinations, etc.) of NMDA antagonists.

However, even though it requires disinhibition of all three excitatory pathways that innervate pyramidal neurons (i.e., the sigma, muscarinic, and kainic acid pathways) to cause toxic reactions in PC/RS neurons, this apparently is not the case for psychotomimetic activities such as hallucinations. The basis for this conclusion is that ibogaine induces disinhibition of only two of the three pathways (the sigma pathway is not disinhibited), yet ibogaine has been known for at least a century to be a hallucinogenic drug.

Interestingly, however, the hallucinations and other psychotomimetic reactions induced by ibogaine have been described by various scientific and other users as a "mystical hallucinatory trance" which is substantially different from the overtly psychotic, schizophrenia-like symptoms induced by other NMDA antagonists such as PCP (angel dust). Therefore, it is reasonable to conclude that the hallucinatory syndrome induced by ibogaine represents a modified and only partial expression of the type of psychotomimetic reactions that are triggered by NMDA antagonists that do not possess sigma receptor antagonist activity.

It follows that if ibogaine has a reduced intensity of psychotomimetic side effects, based on suppression of one of the three excitatory pathways that mediate NMDA antagonist side effects, it is possible to further suppress or totally eliminate the hallucinatory side effects of ibogaine, by blocking either or both of the other two excitatory pathways that activate pyramidal neurons (i.e., muscarinic or kainic acid).

Thus, co-administration of ibogaine together with a muscarinic antagonist, or a kainic acid antagonist (or both, if desired) would provide a means of achieving a high or very high level of blockade of NMDA receptors for neuroprotective therapy (which may be especially useful in critically ill victims of stroke, cardiac arrest, or CNS trauma), while strongly suppressing or totally eliminating any risk of neurotoxic or psychotomimetic side effects.

Muscarinic acetylcholine receptor antagonists which offer good candidates for use as described herein include the anticholinergic agents listed as having high levels of potency in U.S. Pat. No. 5,034,400; such agents include scopolamine, attopine, benztropine, trihexyphenidyl, biperiden, procyclidine, benactyzine, and diphenhydramine.

Numerous kainic acid antagonists (including a number of non-specific non-NMDA antagonists which block both KA receptors and Quis/AMPA receptors) are being actively developed and tested by a number of pharmaceutical companies. Several such agents which have been publicly announced in the literature or at scientific conferences, and which have sufficient potency at KA receptors combined with sufficient ability to penetrate mammalian blood-brain barriers to be therapeutically effective in blocking KA receptors in the CNS after injection into a patient, include NBQX (which is 2,3-dihydroxy-6-nitro-7-sulfamoyl-benzo (F)quinoxaline; see Sheardown et al 1989 and 1990), and GYKI 52466 (which is 1-(amino-phenyl)-4-methyl-7,8-methylendioxy-5H-2,3-benzodiazepine; see Tarnawa et al 1990). In addition, several drug companies involved in this line of research are known to have developed and identified various drugs which have not yet been described in publications, but which permeate the blood-brain barrier and act as KA antagonists in the brain.

Any such drugs which are currently known or hereafter discovered, which have suitable levels of BBB permeability and antagonist activity at either muscarinic or kainic acid receptors in the CNS, are good candidates for coadministration with ibogaine as described herein, to reduce or prevent excitotoxic brain damage.

Two other compounds which are structurally very similar to ibogaine, and which offer good candidates for testing to evaluate their neuroprotective properties in comparison to ibogaine, are ibogamine and tabernanthin. Like ibogaine, both of these are alkaloids isolated from Apocynaceae plants, and they reportedly have neurologically active properties similar to the properties of ibogaine in reducing craving for addictive drugs (see U.S. Pat. Nos. 5,152,994 and 5,026,697, issued to Lotsof). Ibogamine is the basic five-ringed structure; ibogaine is 12-methoxyibogamine (ibogamine with a methoxy group added to the #12 carbon atom), while tabernanthin is 13-methoxyibogamine (ibogamine with a methoxy group on the #13 carbon atom).

Isomers, Salts, and Analogs

Included within the family of agents useful for the purposes described herein are any non-toxic and pharmacologically acceptable isomers, analogs, or salts of ibogaine, ibogamine, or tabernanthin, provided that such isomers, analogs, or salts are functionally and therapeutically effective as NMDA antagonists which do not cause vacuoles or other toxic effects in PC/RS cortical neurons. The neuroprotective potency of any specific isomer, analog, or salt of the listed compounds can be tested using methods such as described in the examples.

The term "pharmacologically acceptable" embraces those characteristics which make a drug suitable and practical for administration to humans; such compounds must be sufficiently chemically stable under reasonable storage conditions to have an adequate shelf life, and they must be physiologically acceptable when introduced into the body by a suitable route of administration. Acceptable salts can include alkali metal salts as well as addition salts of free acids or free bases. Examples of acids which may be employed to form pharmaceutically acceptable acid addition salts include inorganic acids such as hydrochloric acid, sulfuric acid, and phosphoric acid, and organic acids such as maleic acid, succinic acid and citric acid. Alkali metal salts or alkaline earth metal salts might include, for example, sodium, potassium, calcium or magnesium salts. All of these salts may be prepared by conventional means. The nature of the salt is not critical, provided that it is non-toxic and does not substantially interfere with the desired activity. The term "analog" is used herein in the conventional pharmaceutical sense. In general, an analog refers to a molecule that resembles a referent compound but which has been modified in a targeted and controlled manner to replace one or more components of the referent molecule with alternate moieties or other substituents, in a manner that does not destroy a desired and intended function exhibited by the referent molecule. Any coverage of claims which refer to analogs of ibogaine, ibogamine, or tabernanthin is limited to those analogs which exhibit a therapeutically useful suppression of activity at NMDA receptors without causing vacuoles or other toxic effects in PC/RS cortical neurons.

Modes of Administration

Administration of the compounds of this invention to humans or animals can be by any technique capable of introducing the compounds into the bloodstream, including oral administration as described below, intravenous or intramuscular injections, or subcutaneous implantation of slow-release devices or formulations or osmotic mini-pumps. The active compound is usually administered in a pharmaceutical formulation such as in a liquid carrier for injection, or in capsule form for ingestion, although in some acute-care situations any or all of these agents might be injected without a diluting agent. Such formulations may comprise a mixture of one or more active compounds mixed with one or more pharmaceutically acceptable carriers or diluents. If desired, other therapeutic agents may also be present in the formulation, such as streptokinase or tissue plasminogen activator, which help dissolve blood clots in stroke victims.

In some patients who are at high risk of stroke, or who are suffering from a chronic neurodegenerative diseases (such as Parkinson's disease, Huntington's chorea, or Alzheimer's disease) which involves excitotoxicity as one component of the disease process, long-term maintenance-type treatment using oral ingestion of tablets, capsules, or liquids, or transmembrane routes using devices such as lozenges, sublingual tablets or wafers, chewing gum, intranasal sprays, skin patches, permeating lotions or ointments, or rectal suppositories; these devices tend to be preferable for non-physician administration to patients who cannot be relied upon to take their medicine.

Such preparations are all well known in the pharmaceutical arts, and comprise one or more active ingredients as listed above in combination with a pharmaceutically acceptable carrier. In making the compositions, the active ingredient or ingredients will usually be mixed with and diluted by a carrier, or enclosed within a carrier such as a capsule. When the carrier serves as a diluent, it may be a solid, semisolid or liquid material which acts as a vehicle, excipient or medium for the active ingredient. Thus the composition can be in the form of tablets, pills, powders, lozenges, chewing gum, cachets, elixirs, emulsions, solutions, syrups, suspensions, aerosols (as a solid or in a liquid medium), ointments containing for example up to ten percent by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propyl-hydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

For oral administration, the compositions of this invention can be admixed with carriers and diluents molded or pressed into tablets or enclosed in gelatin capsules. Alternatively, the mixtures can be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated or packaged in a unit dosage form, each dosage unit containing an effective amount of ibogaine or a salt, isomer, or analog thereof. The term "unit dosage form" refers to physically discrete units (such as capsules, tablets, or loaded syringe cylinders) suitable as unitary dosages for human subjects and other mammals, each unit containing a predetermined quantity of active material or materials calculated to produce the desired therapeutic effect, in association with the required pharmaceutical carrier. The amount of ibogaine preferred for a unit dosage will depend upon the factors such as the body weight of the patient and the severity of the excitotoxic damage or risk that is at hand. Except when responding to acute events such as stroke, cardiac arrest, or drowning, when higher dosages may be required, the preferred dosage of ibogaine will usually lie within the range of from about 1 to about 50 mg/kg per day if injected and from about 5 to about 100 mg/kg per day if taken orally or rectally. However, it will be understood that the amount of the compound actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

EXAMPLES

Example 1: Studies Showing that Ibogaine Prevents Excitotoxic Neurodegeneration Mediated Through NMDA Receptors A recent report (Popik et al 1994) stated that ibogaine competitively inhibited the binding of radiolabelled MK-801 (dizocilpine maleate) to cell membranes isolated from rat forebrain tissue. Since MK-801 selectively binds to the PCP recognition site in NMDA receptor complexes, this suggests that ibogaine may bind to the same PCP recognition site in the NMDA receptor complex where MK-801 binds. However, this does not indicate whether ibogaine is an agonist or antagonist, or whether it has any net influence or neuroprotective properties that involve the NMDA receptor complex.

To answer those unresolved issues, the Applicant undertook studies involving chick embryo retinal tissue, as described in Example 4 of U.S. Pat. No. 5,034,400 (Olney 1991). Briefly, this assay uses pieces of retinal tissue from chicken embryos, which have mature NMDA and non-NMDA receptors, in tissue culture medium. One of three selective glutamate agonists (NMDA at 80 micromolar concentration; kainic acid (KA) at 20 µM; or AMPA at 15 µM) were used to challenge these tissue samples. Each of these agents selectively triggers neuronal activity via one type of Glu receptor without triggering the other types of Glu receptors. In the absence of a protective NMDA antagonist drug such as MK-801, NMDA-induced excitotoxic overstimulation of the neurons in the retinal tissue causes severe neuronal damage and necrosis within 30 minutes.

Ibogaine was found to block NMDA neurotoxicity, when present at a concentration of 10–25 µM. It showed no blocking activity against KA or AMPA neurotoxicity. This signifies that ibogaine is an NMDA antagonist that can exert neuroprotective activity against glutamate overstimulation, comparable to other NMDA antagonists. It has moderate-to-weak potency, about one tenth as potent as PCP, which blocks NMDA neurotoxicity in this assay at 1–2 µM concentration.

To the best of the Applicant's knowledge, no other evidence has been published demonstrating that ibogaine is, in fact, an NMDA antagonist that can be used to protect against excitotoxic damage or death in neurons.

Example 2: Studies Showing that Ibogaine does not have the Neurotoxic Side Effects Caused by other NMDA Antagonists After analyzing the results of ibogaine that were shown in Example 1, the Applicant undertook a second set of tests in which ibogaine was injected intraperitoneally (ip) into adult female rats at 50 mg/kg. Based on the in vitro potency levels shown in Example 1, this dosage is believed by the Applicant to be ample for providing substantial protection against excitotoxicity, via the NMDA antagonist activity of ibogaine. At this high dose, the ibogaine did not cause any signs of vacuole formation, mitochondrial dissolution, or other cellular damage in the highly vulnerable posterior cingulate and retrosplenial cortical regions, or in any other cortical or limbic regions of the brain that were studied histologically. Separate groups of rats (n=6 per group) were studied by appropriate histological methods to rule out the typical vacuole reaction at 4 hours, heat shock protein expression at 24 hours, or neuronal necrosis at 4 days, following ibogaine injection. None of these detectable signs of neurotoxicity, which are uniformly seen following administration of other NMDA antagonists at neuroprotective dosages, were seen following ibogaine administration.

Example 3: Tests Confirming that NMDA Antagonist Neurotoxcity is Mediated by the Simultaneous Disinhibition of Muscarinic, Sigma and Kainic Acid Receptors As described above, the neural circuitry relevant to the present invention is depicted in a simplified schematic manner in FIG. 1. This depiction shows how glutamate, released by GLU neuron 10, acts via three GABAergic neurons 20, 30, and 40 to sustain tonic inhibition of three excitatory neurons releasing Neuropeptide Y (NPY, neuron 50), glutamate (neuron 60), or acetylcholine (ACh, neuron 70). If the NMDA receptors that govern GABAergic neurons 20, 30, and 40 are blocked by an NMDA antagonist, then the ability of glutamate from neuron 10 to tonically inhibit the three excitatory neurons 50, 60, and 70 is lost, and all three excitatory neurons can begin to hyperstimulate (and thereby injure or kill) pyramidal PC/RS neuron 80.

Pyramidal neuron 80 has three types of excitatory receptors: (1) kainic acid receptors, a type of non-NMDA glutamate receptor; (2) m3 receptors, a type of muscarinic acetylcholine receptor; and, (3) sigma ( ) receptors, which are believed to be triggered by neuropeptide Y (NPY). Since blockade of NMDA receptors apparently abolished Glu-mediated/GABA-mediated inhibitory control over all three excitatory pathways (sigma, muscarinic, kainic acid) that innervate PC/RS cerebrocortical neurons, the Applicant undertook a series of experiments to evaluate the relative importance of each of the three pathways.

In these experiments, combinations of specific receptor agonists were microinjected into the cingulate cortex regions of adult rats, to avoid problems of limited permeability through blood-brain barriers. The three test drugs were: (+)SKF-10,047, an agonist that stimulates activity at sigma receptors; carbachol, an agonist that stimulates activity at muscarinic-type acetylcholine receptors; and kainic acid, an agonist which stimulates non-NMDA glutamate receptors of the kainic acid subtype. In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with any two (or only one) of the three drugs, no such toxic reaction was found.

These results support the circuit diagram depicted in FIG. 1, and they indicate that NMDA antagonist neurotoxicity requires simultaneous hyperactivation of all three of these receptor systems (i.e., sigma receptors, muscarinic acetylcholine receptors, and kainic acid receptors).

A major implication of these results is that, in order to prevent toxic damage to PC/RS cortical neurons by NMDA antagonists, blockade of any one of these three receptor systems (sigma, muscarinic, or kainic acid) can be sufficient.

Example 4: Studies Showing that Ibogaine has a Built-In Safener Mechanism for Protecting Against its Own Neurotoxic Side Effects Based on the Applicant's new and as-yet-unpublished experimental finding (described in Example 3) that it requires excessive activation of all three receptor systems (sigma, muscarinic, and kainic acid) for NMDA antagonist neurotoxicity to occur, the Applicant postulated that the absence of toxic side effects after ibogaine injection (as described in Example 2) might signify that ibogaine, in addition to its NMDA receptor blocking activity, might also exert blocking activity at either a muscarinic, sigma, or kainic acid receptor.

In experiments designed to test this possibility, the Applicant administered ibogaine (50 mg/kg, injected ip) together with a sigma agonist, (+)SKF-10,047 (50 mg/kg subcutaneously). Under this condition, ibogaine consistently caused a very prominent vacuole reaction. In control tests, administering (+)SKF-10,047 (50 mg/kg sc) by itself did not cause a vacuole reaction.

These results, taken together, indicate that (+)SKF-10,047 was able to override the blocking activity of ibogaine at sigma receptors when the two were administered together, but that in the absence of the sigma agonist, the blocking activity of ibogaine at sigma receptors prevented the toxic neuronal side effects of ibogaine's blocking activity at NMDA receptors.

The findings described herein indicate that (1) ibogaine blocks NMDA receptors, thereby causing disinhibition of the three excitatory pathways (muscarinic, sigma, and kainic acid) through which the vacuole reaction is normally mediated; but, (2) the vacuole reaction does not occur, because ibogaine also exerts a blocking action at the sigma receptor.

These results further confirm (1) the conclusion from Example 3 that it requires hyperactivation of all three receptor systems (muscarinic, sigma, and kainic acid) for the neurotoxic reaction to occur, and (2) the corollary conclusion that blockade of only one of those three systems is sufficient to prevent the neurotoxic reaction.

Moreover, these results specifically identify blockade of the sigma receptor as the mechanism by which ibogaine avoids inducing the neurotoxic side effects that other NMDA antagonists predictably cause.

Finally, these results also signify that ibogaine penetrates the blood-brain barrier and enters the CNS in sufficient quantities to effectively block NMDA receptors in a therapeutic manner.

From these discoveries, it follows that ibogaine can be used for neuroprotective therapy against neuronal disorders involving an excitotoxic mechanism. It can be used at high doses without risk of causing toxic side effects in cerebrocortical neurons, provided that it is not coadministered with drugs that activate the sigma receptor system.

REFERENCES

Backonja, M., et al, "Response of chronic neuropathic pain syndromes to ketamine: a preliminary study," *Pain* 56: 51–57 (1994)

Ben-Eliyahu, S., et al, "The NMDA receptor antagonist MK-801 prevents long-lasting non-associative morphine tolerance in the rat," *Brain Research* 575: 304–308 (1992)

Cappendijk, S. L. and Dzoljic, M. R., "Inhibitory effects of ibogaine on cocaine self-administration in rats," *Eur J Pharmacol* 241: 261–5 (1993)

Choi, D. W., "Glutamate neurotoxicity and diseases of the nervous system", *Neuron* 1: 623–634 (1988)

Choi, D. W., "Excitotoxic cell death," *J Neurobiol* 23: 1261–1276 (1992)

Corso, T, et al, "Ethanol-induced degeneration of dentate gyrus, entorhina cortex and other olfactory related areas in rat: effects of co-administration of MK-801, DNQX, or nimodipine," *Soc Neurosci Abst* 18: 540 (1992)

Corso, T. D. et al, "Neuron necrotizing properties of phencyclidine," *Soc Neurosci Abst* 20: 1531 (1994)

Danzebrink, R. M. and Gebhart, G. F., "Antinociceptive effects of intrathecal adrenoceptor agonists in a rat model of visceral nociception," *J pharmacol Exp Therapeutics* 253: 698–705 (1990)

Davar, G., et al, "MK-801 blocks the development of thermal hyperalgesia in a rat model of experimental painful neuropathy," *Brain Res* 553: 327–330 (1991)

Deecher, D. C., et al, "Mechanisms of action of ibogaine and harmaline congeners based on radioligand studies," *Brain Res.* 571: 242–247 (1992)

Ellison, G. and Switzer, R. C., "Dissimilar patterns of degeneration in brain following four different addictive stimulants," *Neuroreport* 5: 17–20 (1993)

Fix, A. S., et al, "Light and electron microscopic evaluation of neuronal vacuolization and necrosis induced by the non-competitive NMDA antagonist MK-801 in the rat retrosplenial cortex," *Exp Neurol* 123: 204–215 (1993)

Glick, S. D., et al, "Effects and aftereffects of ibogaine on morphine self-administration in rats," *Eur. J. Pharmacol.* 195: 341–435 (1991)

Glick, S. D., et al, "Effects of ibogaine on acute signs of morphine withdrawal in rats: independence from tremor," *Neuropharmacology* 31: 497–500 (1992)

Glick, S. D., et al, "Local effects of ibogaine on extracellular levels of dopamine and its metabolites in nucleus accumbens and striatum," *Brain Res.* 628:201–208 (1993)

Grotta, J. t"Safety and Tolerability of the Glutamate Antagonist CGS 19755 in Acute Stroke Patients," *Stroke* 25: 255 (1994)

Hargreaves,i R. J., et al, "Competitive as well as uncompetitive NMDA receptor antagonists affect cortical neuronal morphology and cerebral glucose metabolism," *Neurochem Research* 18: 1263–1269 (1993)

Herrling, P. L. "D-CPPene (SDZ EAA 494), a competitive NMDA antagonist: Results from animal models and first results in humans," *Neuropsychopharmacology* 10, No 3S/Part 1: 591S (1994)

Horvath, Z. and Buzsaki, G, "MK-801-Induced Neuronal Damage in Normal Rats," *Soc Neurosci Abst* 19: 354 (1993)

Kristensen, et al, "The NMDA-receptor antagonist CPP abolishes neurogenic 'wind-up pain' after intrathecal administration in humans, *Pain* 51: 249–253 (1992)

Mao, J, et al, "Intrathecal MK-801 and local nerve anesthesia synergistically reduce nociceptive behaviors in rats with experimental peripheral mononeuropathy," *Brain Res.* 576: 254–262 (1992)

Marek, P., et al, "Excitatory amino acid antagonists (kynurenic acid and MK-801) attenuate the development of morphine tolerance in the rat," *Brain Research* 547: 77–81 (1991)

Massieu, L., et al, "A comparative analysis of the neuroprotective properties of competitive and uncompetitive N-methyl-D-aspartate receptor antagonists in vivo: implications for the process of excitotoxic degeneration and its therapy," *Neuroscience* 55: 883–92 (1993)

McCarthy, D. A., "History of the development of cataleptoid anesthetics of the phencyclidine type," pp. 17–23 in *PCP (Phencyclidine): Historical and Current Perspectives*, Domino, E. F., ed. (NPP Books, Ann Arbor, Mich., 1981)

Neugebauer, V., et al, "The clinically available NMDA receptor antagonist memantine is antinociceptive on rat spinal neurones," *NeuroReport* 4: 1259–1262 (1993)

Olney, J. W., "Glutamate," pp. 468–470 in *Encyclopedia of Neuroscience*, G. Adelman, ed. (Birkhauser, Boston, 1995)

Olney, J. W., "Excitotoxicity and NMDA receptors," *Drug Dev Res* 17: 299–319 (1989)

Olney, J. W., "Excitotoxic amino acids and neuropsychiatric disorders," pp 47–71 in *Annual Review of Pharmacology and Toxicology*, Volume 30, R. George, et al, eds. (Annual Reviews, Inc, Palo Alto, Calif., 1990)

Olney, J. W., et al, "NMDA antagonist neurotoxicity: Mechanism and prevention," *Science* 254: 1515–1518 (1991)

Popik, P., et al, "The putative anti-addictive drug ibogaine is a competitive inhibitor of [$^3$H]MK-801 binding to the NMDA receptor complex," *Psychopharmacology* 114: 672–674 (1994)

Puke, M. J. C. and Wiesenfeld-Hallin, Z., "The differential effects of morphine and the alpha-2-adrenoceptor agonists clonidine and dexmedetomidine on the prevention and treatment of experimental neuropathic pain," *Anesth Analg* 77: 104–109 (1993)

Seltzer, Z., et al, "Modulation of neuropathic pain behavior in rats by spinal disinhibition and NMDA receptor blockade of injury discharge," *Pain* 45: 69–75 (1991)

Sershen, H., et al, "Ibogaine antagonizes cocaine-induced locomotor stimulation in mice," *Life Sci* 50: 1079–86 (1992)

Sershen, H., et al, "Ibogaine reduces preference for cocaine consumption in C57BL/6By mice," *Pharmacol Biochem Behav* 47: 13–19 (1994)

Sheardown, M. J., et al, "NBQX, a specific non-NMDA receptor antagonist, shows neuroprotective effects against cerebral ischemia," abstract published in Proceedings of the First International Conference on Therapy with Amino Acids and Analogs, Vienna, Aug. 7–12, 1989.

Sheardown, M. J., et al, "Blockade of AMPA receptors in the CA1 region of the hippocampus prevents ischaemia induced cell death," pp. 245–253 in Krieglstein, J., and Oberpichler, H., eds., *Pharmacology of Cerebral Ischemia* 1990 (Wissenschaftliche Verlagsgesellschaft, Stuttgart, Germany, 1990)

Tal, M. and Bennett, G. J., "Dextrorphan relieves neuropathic heat-evoked hyperalgesia in the rat," *Neuroscience Letters* 151: 107–110 (1993)

Tarnawa, I., et al, "GYKI 52466, an inhibitor of spinal reflexes, is a potent quisqualate antagonist," pp. 538–546 in Lubec and Rosenthal (eds.), *Amino Acids: Chemistry, Biology, and Medicine* (ESCOM Science Publishers, Leiden, Netherlands, 1990)

Trujillo, K. A. and Akil, H., "Inhibition of morphine tolerance and dependence by the NMDA receptor antagonist MK-801," *Science* 251: 85–87 (1991)

Watkins, J. C., "Excitatory amino acids," pp 37–69 in *Kainic Acid as a Tool in Neurobiology*, McGeer, E., et al, eds. (Raven Press, New York, 1987)

Woolf, C. J., "Recent advances in the pathophysiology of acute pain," *Br J Anaesth.* 63: 139–146 (1989)

Yamamoto, T. and Yaksh, T. L., "Spinal pharmacology of thermal hyperesthesia induced by constriction injury of sciatic nerve: Excitatory amino acid antagonists," *Pain* 49: 121–128 (1992)

Zeigler, D., et al, "Transdermal clonidine versus placebo in painful diabetic neuropathy," *pain* 48: 403–408 (1992)

I claim:

1. A method for treating patients to reduce excitotoxic neuronal damage, comprising the step of administering, to a mammalian patient suffering or at risk of excitotoxic neuronal damage, a pharmacologically acceptable formulation containing at least one neuroprotective drug selected from the group consisting of ibogaine, ibogamine, tabernanthin, and pharmaceutically acceptable isomers, analogs, and salts thereof which penetrate mammalian blood-brain barriers, at a dosage which is therapeutically effective in suppressing glutamate-mediated excitatory activity at NMDA receptors without causing pathologic side effects in cerebrocortical neurons.

2. The method according to claim 1 wherein the neuroprotective drug is administered to the patient in order to reduce or prevent excitotoxic neuronal damage caused by an acute insult to the patient's central nervous system.

3. The method according to claim 1 wherein the neuroprotective drug is administered to the patient in order to reduce or prevent neuronal damage associated with a progressive neurodegenerative disease.

4. The method according to claim 1 wherein the neuroprotective drug is co-administered to the patient along with a second compound which suppresses activity at muscarinic acetylcholine receptors at a therapeutically useful dosage that inhibits hallucinations caused by NMDA antagonist activity.

5. A pharmacological mixture comprising:

(a) a neuroactive drug selected from the group consisting of ibogaine, ibogamine, tabernanthin, and pharmaceutically acceptable isomers, analogs, and salts thereof which penetrate mammalian blood-brain barriers and which suppress glutamate-mediated excitatory activity at NMDA receptors without causing pathologic side effects in cerebrocortical neurons; and, (b) a second compound which suppresses activity at muscarinic acetylcholine receptors, wherein the neuroprotective drug and the second compound in combination are pharmacologically acceptable and are present at therapeutically useful dosages that suppress glutamate-mediated excitatory activity at NMDA receptors, and that also inhibit hallucinations caused by NMDA antagonist activity.

* * * * *